US007309713B2

(12) United States Patent
Rundfeldt et al.

(10) Patent No.: US 7,309,713 B2
(45) Date of Patent: Dec. 18, 2007

(54) USE OF THE NON-OPIATE ANALGESIC DRUG FLUPIRTINE FOR THE TREATMENT OF OVERACTIVE BLADDER AND ASSOCIATED DISEASES INCLUDING URGE INCONTINENCE, URINARY FLOW PROBLEMS AS A RESULT OF PROSTATE HYPERPLASIA AND IRRITABLE BOWEL SYNDROME

(75) Inventors: Chris Rundfeldt, Coswig (DE); Hildegard Kuss, Dresden (DE); Regina Draheim, Radebeul (DE); Katrin Bernoester, Radebeul (DE)

(73) Assignee: Elbion AG, Radebeul (DE)

( * ) Notice: Subject to any disclaimer, the term of this patent is extended or adjusted under 35 U.S.C. 154(b) by 190 days.

(21) Appl. No.: 11/336,406

(22) Filed: Jan. 20, 2006

(65) Prior Publication Data

US 2006/0173052 A1  Aug. 3, 2006

(30) Foreign Application Priority Data

Jan. 31, 2005  (EP) .................................. 05001967

(51) Int. Cl.
  *A61K 31/44* (2006.01)
  *A61P 13/10* (2006.01)
  *A61P 1/00* (2006.01)
(52) U.S. Cl. ...................................... 514/352; 514/867
(58) Field of Classification Search ................. 514/352
  See application file for complete search history.

(56) References Cited

U.S. PATENT DOCUMENTS

| | | | |
|---|---|---|---|
| 3,513,171 A | | 5/1970 | Thiele et al. |
| 3,651,081 A | * | 3/1972 | Sturm et al. .............. 548/362.1 |
| 4,668,684 A | | 5/1987 | Tibes et al. |
| 5,162,346 A | * | 11/1992 | Lobisch et al. .............. 514/356 |
| 5,284,861 A | | 2/1994 | Lobisch et al. |
| 5,503,845 A | | 4/1996 | Goede et al. |
| 6,034,111 A | * | 3/2000 | Pergande et al. ............ 514/353 |
| 6,034,112 A | * | 3/2000 | Pergande et al. ............ 514/353 |
| 6,124,326 A | * | 9/2000 | Pergande et al. ............ 514/352 |
| 6,348,486 B1 | | 2/2002 | Argentieri et al. |
| 6,668,684 B2 | | 12/2003 | Allen et al. |
| 7,160,684 B2 | | 1/2007 | Argentieri et al. |
| 2006/0252104 A1 | | 11/2006 | Argentieri et al. |

FOREIGN PATENT DOCUMENTS

| | | |
|---|---|---|
| DE | 3133519 A1 | 6/1982 |
| DE | 3133519 C2 | 6/1982 |
| DE | 36 04 575 A1 | 8/1986 |
| EP | 0 539 153 A1 | 4/1993 |
| EP | 0 595 311 B1 | 5/1994 |
| EP | 0 615 754 B1 | 9/1994 |
| EP | 0 716 602 B1 | 6/1996 |
| EP | 0 912 177 | 5/1999 |
| EP | 1 072 260 A1 | 1/2001 |
| EP | 1 326 597 B1 | 7/2003 |
| WO | WO 00/59487 | 10/2000 |
| WO | WO 01/39760 | 6/2001 |
| WO | WO 02/00217 A1 | 1/2002 |
| WO | WO-02/32419 A2 | 4/2002 |

OTHER PUBLICATIONS

Derwent abstract 1986-298525; abstracting DE 3545201 (1987).*
Derwent abstract 2002-269313; abstracting DE 10048969 (2002).*
Derwent abstract 2002-442382; abstracting DE 10255415 (2004).*
Derwent abstract 2001-182859; abstracting EP 1242078 (2002).*
Freeman, R.M. et al., "Overactive bladder," Best Practice & Research Clinical Obsterics and Gynaecology, vol. 19(6), pp. 829-841 (2005).*
Medline abstract 2004332451 (2004).*
Snelling, N., "Does any treatment work for irritable bowel syndrome?" International Journal of Osteopathic Medicine, vol. 9, pp. 137-142 (2006).*
Farthing, M.J.G., "Treatment options in irritable bowel syndrome," Best Practice & Research Clinical Gasteroenterology, vol. 18(4), pp. 773-786 (2004).*
Schroeder, et al —KCNQ4 Channel Activation by BMS-204352 and retigabine. (Neuropharmacology (2001).
International Preliminary Report on Patentability issued for PCT/EP2006/000814, Jun. 28, 2007.
Benham, et al.: Acetylcholine activates and inward current in single mammalian smooth muscle cells, *Nature*, vol. 316, pp. 345-347(1985).
Sims, et al.: Antagonistic Adrenergic-Muscarinic Regulation of M Current in Smooth Muscle Cells, *Science*, vol. 239, pp. 190-193 (1988).
Longhurst, et al.: Influence of gender and the oestrous cycle on in vitro contractile responses of the rat urinary bladder to cholinergic stimulation, *British J. of Pharm.*, 131, pp. 177-184 (2000).
Abrams, Describing bladder storage function : overactive bladder syndrome and detrusor overactivity, Urology 62 (Suppl. 5B): 28-37, 2003.
Mertz, Irritable Bowel Syndrome, N,. Eng. J. Med., 349:22; Nov. 27, 2003.
Ford, Do not go gentle—urinary troubles for more than the ageing, Drug Discovery World Fall 2003.
Szelenyi et al., Putative site(s) and mechanisms(s) of action of flupirtine, a novel analgesic compound, Postgraduate Med. J. (1987) 63, 57-50.

(Continued)

*Primary Examiner*—John Pak
(74) *Attorney, Agent, or Firm*—Fulbright & Jaworski L.L.P.

(57) ABSTRACT

The present invention is directed to the prevention, reversal and medical treatment of lower urinary tract dysfunction including bladder instability and other related diseases as described below including urinary flow problems, urgency and incontinence as a result of prostate hyperplasia (BPH) and to the prevention, reversal and medical treatment of irritable bowl syndrome (IBS) with special focus on the diarrhea-predominant and mixed diarrhea-constipation type IBS, both in human beings and animals.

27 Claims, 3 Drawing Sheets

OTHER PUBLICATIONS

Rupalla et al., Flupirtine protects neurons against excitotoxic or ischemic damage and inhibits the increase in cytosolic $Ca^{2+}$ concentration, European J. of Pharmacology 294 (1995) 469-473.

Kornhuber et al., Flupirtine shows functional NMDA receptor antagonism by enhancing $Mg^{2+}$ block via activation of voltage independent potassium channels, J. Neural Transm. (1999) 106: 857-867.

Wein, Pharmacological agents for the treatment of urinary incontinence due to overactive bladder, Exp. Opin. Invest. Drugs (2001) 10(1):65-83.

Dray, The rat urinary bladder, a novel preparation for the investigation of central opioid activity in vitro, J. of Parm. Methods 13, 157-165 (1985).

Friedel et al., Flupirtine, A review of its pharmacological properties, and therapeutic efficacy in pain states, Drugs 45(4): 548-569, 1993.

Swartz et al., Antiparkinsonian effect of flupirtine in monoamine-depleted rats, J. of Neural Transmission (Vienna, Austria:1996), 103 (5) 581-90. Abstract.

Swarz et al., N-methyl-D-aspartate and alpha 2-adrenergic mechanisms are involved in the depressant action of flupirtine in spinal reflexes in rats, European J. of Pharmacology, (Apr. 4, 1995) 276(3) 247-55. Abstract.

Jakovlev et al., General pharmacologic studies on the analgesic flupirtine, Arzneimittel-Forschung (1985) 35(1) 44-55. Abstract.

Otto et al., Efficacy of flupirtine on cognitive function in patients with CJD: a double-blind study, Neurology, (Mar. 9, 2004) 62/5 (714-718). Abstract.

W. Vahlensieck Die stationare urologische Rehabilitation bei interstitieller Cystitis, Urologe-Ausgabe A 2005, Germany, vol. 44. Jan. 1, 2005.

* cited by examiner

A

B

A

B

A

B

USE OF THE NON-OPIATE ANALGESIC DRUG FLUPIRTINE FOR THE TREATMENT OF OVERACTIVE BLADDER AND ASSOCIATED DISEASES INCLUDING URGE INCONTINENCE, URINARY FLOW PROBLEMS AS A RESULT OF PROSTATE HYPERPLASIA AND IRRITABLE BOWEL SYNDROME

This application claims priority from European Patent Application No. 05 001 967.8 filed Jan. 31, 2005, incorporated herein by reference in its entirety.

FIELD OF THE INVENTION

The present invention is directed to the prevention, reversal and medical treatment of lower urinary tract dysfunction including bladder instability and other related diseases as described below including urinary flow problems, urgency and incontinence as a result of prostate hyperplasia (BPH) and to the prevention, reversal and medical treatment of irritable bowl syndrome (IBS) with special focus on the diarrhea-predominant and mixed diarrhea-constipation type IBS, both in human beings and animals.

BACKGROUND OF THE INVENTION

Many people suffer from urinary incontinence. Often, it is believed that incontinence is mainly due to a reduced function of the bladder sphincter (i.e. the muscle keeping the bladder closed) and adjunct parts of the urogenital tract. However, this view is obviously not correct. While under certain circumstances a reduced sphincter function can be found which often is related with a location of the bladder too deep inside the pelvic cavity, this is only one aspect and one possible cause of incontinence. The bladder function can be seen as a delicate balance between the activity of the sphincter and the detrusor, i.e. the muscle which is responsible for getting the urine out of the bladder during voiding and which is represented by the muscular wall of the bladder. Not the malfunction or reduced tension of the sphincter is often the main cause, but rather the imbalance between the tonus of the sphincter and the function of the detrusor.

The bladder detrusor and sphincter combination is one of the two smooth muscle groups which human beings (and also some animals) learn to control directly via central functions while all other smooth muscles are not voluntarily controlled (the other smooth muscle represents the sphincter of the anus). As can be easily understood, this control of the balance involves peripheral and central neuronal functions, to enable the voluntary micturation response. But it also contains in-voluntary components as filling of the bladder finally triggers the urgent need for micturation.

This complex circuit and delicate balance, involving filling of the bladder due to renal function, sphincter activity to keep the bladder close and detrusor activity induced by filling but triggered also by CNS driven nerve function, can easily be disturbed. For example, stress often can result in a need for micturation without an adequate filling of the bladder. Also, the absence of ability to reach a toilet in many persons triggers such an urgency and excessive exaltation such as during laughter can result in in-voluntary voiding.

While these examples indicate how delicate the balance is, this is not a disease. But such disturbances can results in disease stages if the disturbance persists over a long period. The cause for such a disturbance can be manifold. A chronic stress syndrome can result in urgency and incontinence, but also other diseases can cause urgency and ultimately incontinence. Such diseases can be but are not limited to prostate hyperplasia, infections of the urinary tract, different CNS diseases such as Parkinson's disease, Alzheimer's disease, dystonia, anxiety disorders, post traumatic stress syndrome and others. Urge incontinence or inadequate urgency is also a frequent side effect of neuroleptic treatment.

It is to be noted that the disease is not the incontinence which only is a possible symptom but rather the un-physiological urgency, i.e. the need to go to the toilet despite the fact that that would not be necessary on the basis of filling of the bladder. Such diseases may be related to morphological changes in the urinary tract such as hyperplasia or hypertrophy of the bladder wall, inflammation or hypertrophy of the mucosa, miss-placement of the bladder or morphological changes in other parts of the urogenital tract such as prostate or urethra, but in many cases no morphological changes can be found as functional changes including functional changes in the central control of micturation may be the underlying cause. This is especially the case in children suffering from overactive bladder and ultimateively from incontinence (mostly nocturnal incontinence) which can be a big problem for both, children and families.

According to a comprehensive review of terminology of lower urinary tract function/dysfunction, the International Continence Society (ICS) has recommended the use of the terms overactive bladder syndrome (OAB) and detrusor overactivity for this group of diseases. Detrusor overactivity is defined as a urodynamic observation characterized by involuntary detrusor contractions during the filling phase that may be spontaneous or provoked. Detrusor overactivity is subdivided into idiopathic detrusor overactivity and neurogenic detrusor overactivity. Because detrusor overactivity is a urodynamic diagnosis, it is possible to record symptoms and signs during urodynamic studies to correlate them with any involuntary contractions. The ICS 2002 report describes 2 types of detrusor overactivity: (1) phasic, which may or may not lead to urinary incontinence; and (2) terminal, which is a single involuntary detrusor contraction that often results in complete bladder emptying. OAB, as defined by ICS 2002, is a new term and is a symptomatic diagnosis. OAB is defined as urgency, with or without urge incontinence, and usually with frequency and nocturia.

A more general term used is lower urinary tract dysfunction. This all inclusive term applies to a cluster of distinguishable disorders however with common or largely overlapping symptomatology whose definitions continue to evolve as they become better understood. The symptoms are:

Urge or urgency (intense sensing that the bladder has reached its threshold)

Frequency of urination (8 ore more times per day)

Nocturia (sleep disturbance accompanying the need to urinate)

In some cases, obstruction of urine flow

In other cases, urinary incontinence

Urogenital or pelvic pain

Disorders which are grouped under the term lower urinary tract dysfunction include:

Stress urinary incontinence (inability to prevent leakage of urine during activities that increase abdominal pressure)

Urge urinary incontinence: Incontinence episodes driven by detrusor overactivity Mixed urinary incontinence (a mixture of both)

Overactive bladder syndrome: An inclusive term which not only included the above mentioned ones but also the "dry" overactive bladder without incontinence but with urgency, urinating frequency and nocturia. Overactive bladder is also seen frequently in children resulting in urgency, nocturia, and incontinence. Even in children, often pharmacological treatment is indicated to prevent incontinence, especially during the night (C. Persspm de Geeter 2004, Der Urologe Volume 7, page 807ff).

Benign prostatic hyperplasia/lower urinary tract symptoms: urinary storage difficulties typical of OAB plus obstruction of urinary flow, coincident with enlargement of prostatic mass Neurogenic bladder: Catastrophic loss of bladder control on patients with spinal cord injury, stroke, multiple sclerosis, Parkinsons disease and other CNS diseases.

All these diseases have one keys symptom in common: an imbalance of detrusor activity and sphincter activity of the bladder. In addition, all diseases are not primarily smooth muscle diseases, but rather are nervous system diseases as this delicate balance is established and maintained by central and peripheral nervous system activity.

While all the mentioned diseases relate to bladder function, a very similar situation can be found in a different disease, the irritable bowel syndrome (IBS). In IBS patients, a dys-regulation of gut function is central to the disease. While in most patients, this results in hypermotility and diarrhea, in others it results in hypomotility and constipation while in again other both, diarrhea and constipation can be observed. IBS is due to these colonic symptoms classified as either diarrhea predominant, constipation predominant or mixed type. While pain including abdominal pain is part of IBS symptomatology, it is to be noted that this invention is not directed to the pain as a secondary symptom of this disease but to the dys-regulation of gut function. However, in all these cases the disturbance can be expected to be found in the nerval control of the gut activity, i.e. in the intestinal nervous system and the control thereof. Current treatment of IBS often includes a combination of antidiarrheals, antispasmodics, and sometimes antidepressants.

The aim of the treatment in both cases, lower urinary tract dysfunction and IBS, is to restore the balance and to normal function focussing either on the nervous system control or directly on the smooth muscle function.

Lower urinary tract dysfunction is a very common disease with high prevalence, but often neglected. The prevalence of overactive bladder increases with age, ranging from 4.8% in females below age of 25 to 30.9% in those >65 years of age (P. Abrahams 2003, Urology Volume 62, Supplement 5B, page 28ff). Similar prevalence's can be found in male patients over the age of 65, however due to BPH. The prevalence of the other diseases are somewhat lower.

IBS, likewise, is also a very common disease and is also often neglected. The prevalence of IBS was found to be 12% among adults in the USA. The prevalence world wide can be expected to be similar (H. R. Mertz. Irritable bowel syndrome (Review article); New England Journal of Medicine 349:2136-46, 2003). New treatment is urgently needed since currently available, mostly symptomatic treatment is often insufficient and not free of side effects.

Current Treatment

Current treatment is mainly based on anticholinergic drugs, i.e. drugs which block the muscarine receptors. Such a pharmacological intervention is not entirely satisfactory. While the pharmacological effect, being statistically significant, may not be strong giving a 30% reduction in number of daily micturations only (getting the patients down from 15 times to approximately 11 times per day) even this small effect is associated with unpleasant side effects including mouth dryness, dry eyes and dry skin, constipation, and negative effects on cognition and memory. Other side effects include blurred vision and problems to accommodate. Further, central aspects of the disease, i.e. the urgency, is even less treated with such compounds. Currently, newer drugs with selectivity to the M3 subtype of the muscarine receptor, are about to be marketed. While the claim is, that they have a better separation between side effects and effects, this may not be fully correct. Constipation seems to be even a larger problem and efficacy is not improved. As the M3 receptor is also present in the eye, blurred vision and accommodation problems may remain.

Other drugs used include antidepressants, alpha1 adrenoceptor antagonists, and, for BPH only, 5alpha reductase inhibitors. Newer targets tested include 5HT receptor antagonists, potassium channel openers, and other targets. A list of targets currently evaluated in clinical trials can be found in an article from A. P. Ford, Drug Discovery World, Issue Fall 2003, page 9-17, which is herein incorporated by reference.

While current treatment for IBS often focuses on anti-diarrheals and antispasmodics, sometimes even antidepressants, anticholinergic drugs used for the treatment of incontinence are also active as they are good antidiarrheal agents. Newer drug targets include among others modulators of calcium activated potassium channels.

Based on this data review, we can conclude, that there is a well defined medical need for the development of new drugs for the treatment of OAB, and also more general for the treatment of lower urinary tract dysfunction. There also is an urgent need to for the development of newer drugs for the treatment of IBS. Such drugs should better address the over-activity which is a key symptom of both, IBS and OAB, without reducing the ability of the bladder detrusor to contract fully (in the case of OAB). This differentiation is essential. Drugs which are just relaxing smooth muscles often can also relax the detrusor muscle (and the sphincter muscle). Such relaxation, for example induced by calcium antagonists, may be active, but does result in two different risks. On one hand, the reduced contraction force can lead to residual volume remaining in the bladder. Such residual volume can be the cause not only for chronic infections but also for formation of cystic calculi. On the other hand, a plain smooth muscle relaxation also will relax the sphincter. In this case, the balance between sphincter activity and detrusor activity may not be positively influenced. Therefore, calcium antagonists are not in use for treatment of incontinence. Instead, calcium antagonists such as Diltiazem are used for the treatment of hypertension and angina pectoris due to their general effects to relax smooth muscles including vascular smooth muscles. Other drug targets are being evaluated, such as potassium channel openers with a focus on openers of the ATP sensitive potassium channel. However, while potent effects in models of hyperreactive bladder can be achieved, such drugs can not be used since they also relax smooth muscles of the vascular bed resulting in strong effects on blood pressure. Therefore none of these drug candidates has yet made it into a successful drug.

New drugs for the treatment of OAB should be active on the bladder detrusor activity without reducing the contraction force, should not or only slightly be active on vascular smooth muscles to avoid unwanted effects on blood pressure and should be safe with regard to other side effects including all cardiovascular side effects. New drugs for the treatment of IBS should normalize the activity of the overactive intestine without paralyzing the smooth muscle, i.e. they should not interfere with the ability of the gut to contract but rather interfere with the control of the gut motility.

DESCRIPTION OF THE INVENTION

We have tested flupirtine in an animal model of lower urinary tract dysfunction focussing on detrusor activity and urge incontinence in rats. The selected model represents a setup where the interplay of the central nervous system activity and the smooth muscle (detrusor) activity can be observed. The model also is predictive for effects in IBS.

Unexpectedly, we have found that flupirtine was very active in suppressing spontaneous detrusor contractions induced by infusion of warm saline into the bladder of the anaesthetized rat. The potency of flupirtine with regard to the frequency of contraction was largely comparable to the used reference compounds oxybutynin, which is a compound often clinically used for the treatment of OAB and incontinence, and duloxetine (Yentreve®/Ariclaim®), which is a new drug used for the treatment of moderate to severe stress urinary incontinence (SUI) in women. In contrast to oxybutynin flupirtine did not exert the unwanted effect on the contractility force leaving the maximal contraction not affected, while oxybutynin treatment lead to a substantial reduction in contraction force as can be seen in a reduction in recorded amplitude of the contraction. Also at higher doses a paradox increase in contraction frequency could be observed with oxybutynin resulting in an even higher contraction rate compared to the control measurement. In the case of duloxetine, on the other hand, the contraction force was slightly reduced at a dose of 3.0 mg/kg only, while at lower or higher doses of administration the maximal contraction was not affected. At the dose of 3.0 mg/kg, however, a slight increase in contraction frequency could be observed with duloxetine as well.

The data thus may be summarized that flupirtine was found to be very active in this animal model predictive for effects on detrusor overactivity. In addition, flupirtine did not cause the unwanted effects observed with the reference compounds duloxetine and the clinically used drug oxybutynin, i.e. increase in frequency at higher doses and effects on contraction amplitude. Flupirtine did also not cause any effect on peripheral blood pressure. The first effects of flupirtine became visible at intraduodenal doses of 3 mg/kg. These doses are lower than doses reported to exert analgesic effects in the same species, i.e. the rat. This indicates that the pharmacological effect of flupirtine is to be expected to be seen at doses which are very well tolerated. The doses needed to exert the wanted effects on the bladder detrusor activity can be expected to be lower or in the same range as doses used for analgesia in man. A detailed description of the experiment is given below in the Example.

A different model of bladder hyperactivity/detrusor instability induced by chronic partial outflow obstruction is also useful to evaluate the efficacy of a compound. Partial obstruction is achieved using partial ligation of the proximal urethra in rats. Within 6 weeks, this results in pronounced bladder instability and increased bladder wall thickness. This can be recorded using cystometry. This model more closely resembles the situation during prostate hyperplasia and other diseases resulting in outflow obstruction. Flupirtine is also active in this model.

Flupirtine was also tested in an in vitro model of detrusor muscle activity. In this model, isolated organ strips of rat bladder was introduced in an isolated organ bath system. Contraction of the bladder muscle strip was induced by application of potassium chloride (40 mM) and the relaxant effect of flupirtine was tested to determine the IC50, i.e. the concentration of flupirtine needed to counteract the contractile response of potassium chloride by 50%. In this model, flupirtine did show some activity, but the concentration needed to relax the bladder strip was rather high. The IC50 amounted to 7.5 µM which is well above the concentration reached after intraduodenal administration of 3 mg/kg in rats. These data indicate, that the main target for pharmacological action can be expected to be the nervous system controlling the bladder function. Direct effects on the bladder wall may be of limited relevance for the pharmacological effect. Indeed, this is in line with the observation that the contraction force of the detrusor in above mentioned in vivo models was not influenced at doses which clearly had pharmacological effects on micturation frequency.

Flupirtine, a triaminopyridine compound with antinociceptive effects, is marketed in Germany and some other countries for the treatment of centrally mediated pain under the trademark Katadolon™. It is an analgesic that has been used in Europe to treat pain association with surgery, cancer, trauma, dental pain, degenerative rheumatic arthrosis, inflammatory rheumatoid arthritis, interstitial cystitis and liver disease. It acts via central nervous system through nonopiate pain pathways, possibly involving the thalamus or spinal pain pathways. In some, but not all, studies flupirtine has been found to be as effective as opiates in relieving pain. Moreover, flupirtine offers a clear advantage over opiates in that it is not addictive and there have been no reports of abuse. The drug is very well tolerated and is free of effects on the cardiovascular system in patients.

The mechanism of this drug is not well understood. While the compound is positioned as centrally acting-non-opioid analgesic with some muscle relaxant property, several different mechanisms of action have been proposed. Early work based on antagonism studies concluded that the antinociceptive activity of flupirtine is due to activation of descending noradrenergic pathways (Szelenyi and Nickel, Postgrad Med J. 1987; 63 Suppl 3:57-60). Later work concluded that flupirtine limits the calcium influx of cells resulting, among other effects, in neuroprotection (Rupulla et al., Eur J. Pharmacol. 1995 Dec. 29; 294(2-3):469-73). Again other authors concluded that flupirtine acts as a functional NMDA antagonist by enhancing the magnesium mediated block of the NMDA receptor (Kornhuber et al., J. Neural Transm. 1999; 106(9-10):857-67). Other mechanisms proposed are activation of G-protein coupled inwardly rectifying potassium current. It was also published to act as a positive GABA modulator. Based on these available data, a specific mechanism of action of flupirtine is not yet identified and the complex pharmacology may be due to the concert of different mechanisms of action.

Several patent documents relate to the use of flupirtine. Early work focussed on the analgesic activity. This was lately extended to the use of flupirtine for the treatment of canine and feline arthritis (EP-A-1 242 078). In view of its analgesic properties flupirtine has also been used for the treatment of interstitial cystitis (Vahlensieck, Urologe [A] 2005; 44:41-45). Combination therapy of flupirtine and morphine was also claimed to further improve the analgesic activity (EP-A-0 595 311).

Lateron especially neuroprotective effects and cytoprotective effects were published in several patents, for example in EP-A-0 716 602, DE-A-196 25 582, and EP-A-0 912 177. This was extended to disorders in, e.g. myocardial infarction, renal shock or pulmonal shock, in EP-A-0 912 177. A different therapeutic target was defined to be the haematopoietic system, e.g in DE-A-195 41 405 or EP-A-0 859 613. Other diseases to be treated with flupirtine include tinnitus, e.g. DE-A-100 48 969 muscular tension, e.g. EP-A-0 659 410, fibromyalgia and related conditions, e.g. WO 00/59487, Batten disease, e.g. WO 01/39760, or Parkinson disease, e.g. U.S. Pat. No. 5,284,861. Furthermore different dosage and administration forms, are described in DE-A-102 55 415, or EP-A-0 615 754.

However, despite of the widespread use and examination of flupirtine, it has not previously been known to be useful for the treatment of lower urinary tract dysfunction or IBS. The present invention is based upon the finding that flupirtine is unexpectedly effective in treating, inhibiting or preventing IBS and lower urinary tract dysfunction.

Chemical Form of Flupirtine

The present invention is not limited to any particular chemical form of flupirtine and the drug may be given to patients either as a free base or as a pharmaceutically acceptable derivative, e.g. an acid addition salt or an amide. For example, the hydrochloride and maleic salts are generally preferred but other salts derived from pharmaceutically acceptable organic or inorganic acids may be also used. Examples of such acids include, without limitation, hydrobromic acid, phosphoric acid, sulphuric acid, methane sulfonic acid, phosphorous acid, acetic acid, tartaric acid, lactic acid, succinic acid, citric acid, malic acid, aconitic acid, salicylic acid, phthalic acid, embonic acid, enanthic acid, and the like. Furthermore, amides of flupirtine with pharmaceutically acceptable acids, particularly amides with carboxylic or sulfonic acids may be used. The preparation of flupirtine, 2-amino-3-carbethoxyamino-6-(4-fluorobenzylamino)-pyridine, and its physiologically acceptable salts is described in German patents DE-1,795,858 and DE-3,133,519.

Dosage

The total daily dosage of flupirtine administered to a patient should be at least the amount required to prevent, reduce or eliminate one or more of the symptoms associated with lower urinary tract dysfunction or IBS, preferably the urgency and the frequency of daily micturations with respect to lower urinary tract dysfunctions and the diarrhea related symptoms in IBS.

The typical daily dosage particularly for use in humant patients will be between 50 and 1000 mg, in general, e.g. between 100 mg and 400 mg calculated on the basis of the free base form of flupirtine. Higher doses are tolerated by some patients and daily dosages of 2,000 mg or more may be considered in refractory cases or in patients receiving concomitant drug treatment with agents may lower the serum concentration and half-life of flupirtine (e.g., cytochrome P450 inducing compounds such as carbamacepine, phenyloin, phenobarbital and rifampin) as well as in cigarette smokers. In contrast, elderly patients, patients with renal or hepatic dysfunction, and patients receiving concomitant drugs which inhibit the cytochrome P450 system should receive lower initial and maintenance doses, e.g., 25 to 200 mg.

These dosage are simply guidelines and the actual dose selected for an individual patient will be determined by the attending physician based upon clinical conditions and using methods well-known in the art. Flupirtine may be provided in either a single or multiple dosage regimen or on an as-needed regime. Examples are: a patient may take 100 mg of flupirtine orally three times a day or alternatively 200 mg of flupirtine twice a day. A once daily administration may also be possible, based on the individual symptoms and the extend and duration of relief achieved. A controlled release formulation as described in EP-A-0 615 754, a cutaneous form as described in DE-A-102 55 415 or other formulations may as well be used, but a clinical effect in the said diseases is not dependent on the use of these specific dosage forms.

Dosage Forms and Route of Administration

Any route of administration and dosage form is compatible with the present invention and flupirtine may be administered as either the sole active agent or in combination with other therapeutically active drugs. Although compositions suitable for oral delivery are preferred, other routes that may be used include peroral, internal, pulmonary, rectal, nasal, vaginal, lingual, transdermal, intravenous, intraarterial, intramuscular, intraperitoneal, intracutaneous and subcutaneous routes. Specific dosage forms include tablets, pills, capsules, powders, aerosols, suppositories, skin patches, parenterals, and oral liquids including oil aqueous suspensions, solutions and emulsions. Sustained release dosage forms may be used. All dosage forms may be prepared using methods that are standard in the art (see e.g., Remington's Pharmaceutical Sciences, 16th ed., A. Oslo Editor, Easton Pa. (1980)). Specific guidance for the preparation of dosage forms for various routes of delivery is provided by U.S. Pat. Nos. 4,668,684; 5,503,845; and 5,284,861.

Flupirtine may be used in conjunction with any of the vehicles and excipients commonly employed in pharmaceutical preparations, e.g., talc, gum arabic, lactose, starch, magnesium stearate cocoa butter, aqueous or non-aqueous solvents, oils, paraffin derivates, glycols, ets. Coloring and flavouring agents may also be added to preparations, particularly to those for oral administration. Solution can be prepared using water or physiological compatible organic solvents such as ethanol, 1,2-propylene glycol, polyglycols, dimenthyl sulfoxide, fatty alcohols, triglycerides, partial esters of glycerine and the like. Parenteral compositions containing flupirtine may be prepared using conventional techniques and include sterile isotonic saline, water, 1,3-butanetiol, ethanol, 1,2-propylene glycol, polyglycols mixed with water, Ringer's solution, etc.

Medical Indications

The invention is useful for inducing, assisting or maintaining desirable bladder control or gut function control, respectively, in a mammal experiencing or being susceptible to bladder instability or urinary incontinence or, more generally, lower urinary tract dysfunction or IBS. The invention also includes prevention, treatment or inhibition of recurrence of symptoms after a period of symptoms (relapse prophylaxis). Symptoms may be lower urinary tract dysfunction, bladder-related urinary conditions and bladder instability, urinary urgency, including nocturnal enuresis (bedwetting), nocturia, voiding dysfunction, and urinary incontinence. Also treatable or preventable is bladder instability secondary to prostate hypertrophy and other diseases causing such symptoms as part of the symptomatology, such as Parkinson's disease, Alzheimer's disease and other diseases. Flupirtine is also useful in promoting the temporary delay of urination whenever desirable. The invention may also be utilized to stabilize the bladder and treat or prevent incontinence with urge urinary incontinence, stress urinary incontinence, or a combination of urge and stress incontinence in a mammal, which may also be referred to as mixed urge and stress incontinence. The invention also includes assistance in preventing or treating urinary incontinence associated with secondary conditions such as prostate hypertrophy.

The invention may be utilized to allow a recipient to control the urgency and frequency of urination. The invention includes the treatment, prevention, inhibition and amelioration of urge urinary incontinence, also known as bladder instability, neurogenic bladder, voiding dysfunction, hyperactive bladder, detrusor over-activity, detrusor-hyper-reflexia, or uninhibited bladder.

As described above, the invention includes treatment, prevention, inhibition or amelioration of symptoms of hyperactive of instable bladder, neurogenic bladder or hyperreflexic bladder. These uses include, but are not limited to, those for bladder activities and instabilities in which the urinary urgency is associated with prostatitis, prostatic hypertrophy, interstitial cystitis, urinary tract infections or vaginitis. The invention may also be used to assist in inhibition or correction of the conditions of Frequency-Urgency-Syndrome, and lazy bladder, also known as infrequent voiding syndrome. The invention is directed to treating lower urinary tract dysfunctions by exerting an effect on the respective diseases and/or conditions instead of providing analgesic activity only, and does therefore not comprise pain treatment in interstitial cystitis. Preferably, the lower urinary tract dysfunction does not comprise interstitial cystitis.

Further, the invention may be used to treat, prevent, inhibit, or limit the urinary incontinence, urinary instability or urinary urgency associated with or resulting from administration of other medications, including diuretics, vasopressin antagonists, anticholinergic agents, sedatives or hypnotic agents, narcotics, alpha-adrenergic agonists, alpha-adrenergic antagonists, or calcium channel blockers.

Furthermore, the invention is useful for inducing or assisting in urinary bladder control or preventing or treating the maladies described herein in humans in need of such relief, including adults and pediatric uses. However, it may also be utilized for veterinary applications, particularly including canine and feline bladder control methods. If desired, the invention may also be used with other pet animals or farm animals, such as ovine, porcine and equine breeds.

The invention are also useful for the treatment or preventable of symptoms of IBS, especially with a focus on diarrhea and hypermotility related symptoms.

Method of Treatment

Flupirtine is very well tolerated. Thus, the proposed effective dose may be given making no titration of the possibly effective dose necessary for safety reasons. However, based on the good activity in the disease models, one may start with a low dose. A patient may be initially given a low dose of flupirtine, e.g., 100 mg per day. Although flupirtine is relatively safe when used at dosages lower than 600 mg per day, a number of side effects have been reported. Among these are dizziness, drowsiness, puritus, dry mouth, and, less frequently, nausea, depression, sleep disturbance, and headache. If adverse effects are not experienced by the patient and if a full control of the symptoms is not achieved with the initially selected dose, dosage may be gradually increased until a satisfactory alleviation of the symptoms is achieved. Since flupirtine is non-addictive, treatment may be safely maintained over a prolonged period of time.

The daily dose of flupirtine may be administered as a single tablet or capsule, but it is generally preferable to divide the daily dosage into two or more separate aliquots. Alternatively, a patient may simply take flupirtine as needed, up to the maximum tolerated daily dosage. Flupirtine administration may be combined with the administration of other therapeutically active agents, such as anticholinergic drugs or, in case of IBS, also antidepressants and other CNS active drugs, depending upon the individual needs of a patient.

Such combination therapy of flupirtine with other agents used to treat the above diseases is of special interest since treatment with flupirtine benefits addi from combination treatment with compounds commonly used in these diseases. Examples for such combinations comprise muscarine receptor agonists in the case of detrusor hyperactivity and 5-alpha-reductase inhibitors in the case of prostate hyperplasia, spasmolytics and antidepressants as used in case of IBS. In addition to these compounds, other commonly used compounds for the treatment or prevention of symptoms in such disease stages are also well suitable for combination therapy. As the molecular target of flupirtine is neither the muscarine receptor nor the enzyme 5-alpha reductase or other targets of pharmacologically active drugs, an at least additive effect can be expected for any such combination therapy.

EXAMPLE

Figure 1:
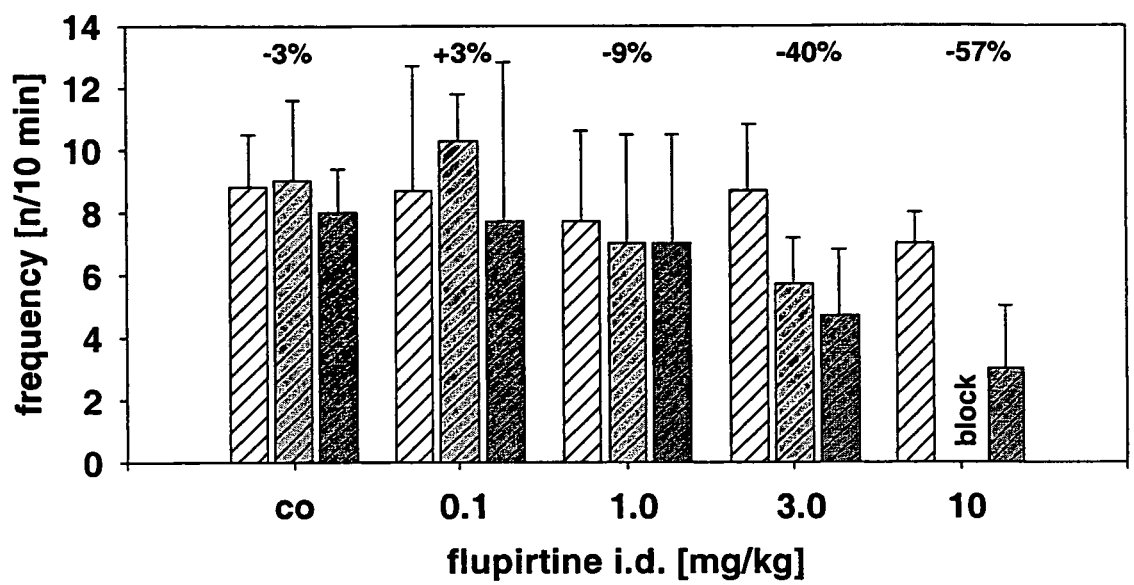
FIG. 1: Effects of different intraduodenal (i.d.) doses of flupirtine maleate on the frequency [n/10 min] (A) and the amplitude [mm Hg] (B) of the rhythmic bladder contractions. Bars represent the mean number of peaks [n/10 min]=frequency (upper, hatched bars), or the mean height of the peaks [mm Hg]=amplitude (lower, non hatched bars) with their standard deviations (sd), recorded 'pre'=☐ and 'post'=▨ 20-30 min; ■ 50-60 min, co=control group. Values above the bars are mean change in percent from base value (Δ%).
Figure 1:
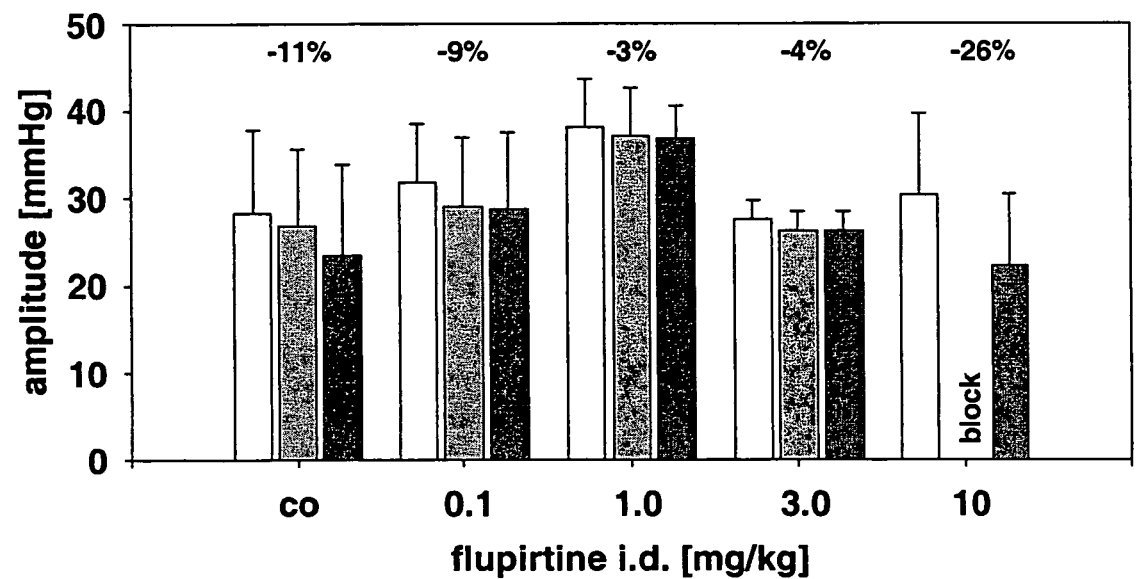

Flupirtine in a Rat Model of Overactive Bladder (OAB)

1 Introduction

Overactive bladder (OAB) is a serious condition for which no effective treatment without undesirable side effects exists today. OAB is often cause of urinary incontinence but can be frequently seen also without incontinence as urgency syndrome. OAB may be a symptom of a complex disease such as benign prostate hyperplasia or Parkinson's disease, but exists also as a disease of its own. OAB can be seen in humans at all ages including children and elderly.

If conservative management forms of treatment fail, pharmacotherapy, currently in most cases in the form of anticholinergic drugs (e.g. oxybutynin hydrochloride) is initiated. Oxybutynin hydrochloride, a drug with both anticholinergic and calcium antagonistic effects, decreases peripherally bladder contractility, but side effects like inhibition of saliva production and increased residual urine content are present (Wein, Exp. Opin Invest Drugs 10:65-83, 2001).

In the search for new drugs compounds are of interest which affect the central nervous system circuits involved in micturation as well as the peripheral nerves resulting in a decrease in the frequency of the voiding reflex without any effect on bladder contractility. In search for drugs for the treatment of lower urinary tract dysfunction with focus of OAB, we have established an animal model to evaluate possible drug candidates. The method utilises spontaneous, volume-induced contractions of the urinary bladder in anaesthetised rats and was developed and first described by Dray (J. Pharmacol. Meth. 13:157-165, 1985) to assess the central activity of substances with opioid properties on bladder function. As this model clearly mimics the interplay between smooth muscle function and neuronal control thereof, this model can be also used to predict drug effects in a different disease, i.e. irritable bowl syndrome (IBS).

A centrally acting drug compound is duloxetine (Yentreve®/Ariclaim®) which was recently introduced in the EU market for the treatment of moderate to severe stress urinary incontinence (SUI) in women (Lilly and Boehringer Ingelheim). The cellular/molecular mechanism of duloxetine is a centrally acting selective inhibitor of serotonin (5-HT) and norepinephrine reuptake.

Flupirtine maleate (Katadolon™) is another centrally acting non-opioid analgesic drug. The mechanism of Flupirtine is by no means fully understood. While it was published to have functional or direct antagonistic effects on glutamatergic neurotransmission with focus on NMDA receptor function, other have found that the compound has $GABA_A$ agonistic properties and increases potassium conductance (Friedel and Fitton, Drugs 45:548-569, 1985). In addition, flupirtine maleate was shown to have a musculutropic-spasmolytic effect if administered at high concentrations in vitro.

To evaluate whether flupirtine maleate may be active in lower urinary tract dysfunction (here termed, for the ease of use only, overactive bladder) and also, whether flupirtine may also be active in IBS, we have tested this compound in the rat model of OAB.

Aim of the study: To characterise the effects of the analgesic flupirtine maleate on the bladder function we used the model volume-induced contractions of urinary bladder in urethane anaesthetised rats. Oxybutynin hydrochloride and duloxetine hydrochloride were tested as reference. The compounds at the dose range 0.1-10 mg/kg were intraduodenally administered to anaesthetised rats. The intraduodenal route was chosen to mimic the oral route and to avoid the use of solvents necessary for intravenous administration.

2 Materials and Methods 2.1 Animals
  Species: Sprague Dawley rat
  Sex: Female
  Body weight: 200-270 g
  Breeder: Charles River, Sulzfeld
  Food/Tap water: pellets, ssniff M/R15, ad libitum, Spezialdiäten GmbH, Soest/Wesffalen, FRG
  Conditions in animal housing: Rats were kept conventionally in groups of 6 in macrolon cages No. 4.
  Room temperature: 20-24° C.
  Relative humidity: 40-70%, deviations from the maximum range caused during cleaning procedure are possible
  Light/Dark rhythm: 12/12 h light/dark cycle, light on at 6:00 a.m.

The food was withdrawn 16 hours before intraduodenal drug administration. Tap water was available ad libitum.

2.2 Chemicals
  Test compound: Flupirtine maleate
  Chemical name: [(2-Amino-6-(4-fluorophenyl)-methyl-amino-3-pyridinyl)-carbamicacid ethylester maleate]
  Manufacturer: ASTA Medica GmbH, Frankfurt, FRG
  Mol. Weight of flupirtine maleate: 420.4 g/mol
  Mol. Weight of flupirtine free base: 304.33 g/mol
  Reference compound: Oxybutynin hydrochloride
  Chemical name: (α-Phenylcyclohexaneglycolicacid 4-[diethylamino]-2-butynyl ester hydrochloride
  Manufacturer: Sigma Chemie Deisenhofen, FRG
  Mol. Weight of oxybutynin HCl: 394.0 g/mol
  Mol. Weight of oxybutynin free base: 357.54 g/mol
  Reference compound: Duloxetine hydrochloride
  Brand name: Yentreve®, Ariclaim®
  Chemical name: (+)-(S)-N-Methyl-N-[3-(naphthalen-1-yloxy)-3-(2-thienyl)propyl]amine hydrochloride
  Manufacturer: Boehringer Ingelheim Pharma GmbH & Co. KG, Ingelheim, FRG
  Batch: A069673A, usable to 03/2006
  Mol. Weight of duloxetine HCl: 333.88 g/mol
  Mol. Weight of duloxetine free base: 297.38 g/mol Vehicle:
  Chemical name: hydroxyethylcellulose (tylose)
  Supplier: Merck-Schuchardt, Hohenbrunn, FRG Anaesthetic:
  INN: urethane
  Supplier: Sigma Chemie, Deisenhofen, FRG
  Route of administration: subcutaneous
  Dose: 1.25 g/kg bw.

2.3 Drug Administration Schedule/Dosage

| | Applied volume: 0.4 ml/100 g body weight (b.w.) | | | | |
|---|---|---|---|---|---|
| Substance | Dose (mg/kg) | Route of appl. | Vehicle | Pre-treatment | Observation period (h) |
| Flupirtine maleate | 0.1; 1; 3; 10 | i.d. | tylose | no | 1 |
| Oxybutynin hydrochloride | 0.1; 1; 10 | i.d. | tylose | no | 1 |
| Duloxetine hydrochloride | 0.1; 1; 3; 10 | i.d. | tylose | no | 1 |

Conversion of tested dose in mg/kg b.w. into the content of free base and molar amount/kg body weight:

| Substance | Dose of salt form used in test mg/kg b.w. | Content of free base mg/kg b.w. | Molar amount μmol/kg b.w. |
|---|---|---|---|
| Flupirtine maleate | 0.1 | 0.072 | 0.24 |
|  | 1.0 | 0.72 | 2.37 |
|  | 3.0 | 2.17 | 7.11 |
|  | 10 | 7.24 | 23.7 |
| Oxybutynin hydrochloride | 0.1 | 0.091 | 0.25 |
|  | 1.0 | 0.91 | 2.54 |
|  | 10 | 9.07 | 25.4 |
| Duloxetine hydrochloride | 0.1 | 0.089 | 0.30 |
|  | 1.0 | 0.89 | 3.0 |
|  | 3.0 | 2.67 | 9.0 |
|  | 10 | 8.9 | 30 |

Preparation of Test Compounds for Intraduodenal Administration as a Suspension:

Flupirtine maleate or oxybutynin hydrochloride were suspended in hydroxyethylcellulose (0.5%) in demineralised water. The substances were ground in a mortar with pistil. The suspensions were placed on a magnetic stirrer before and during dosing procedures. The substances were freshly prepared in the morning and applied intraduodenally in a volume of 0.4 ml/100 g body weight. Control rats received hydroxyethylcellulose (0.5%) i.d.

For the preparation of the duloxetine hydrochloride suspension the content of commercially available Yentreve® 40 mg hard gastro-resistant capsules containing duloxetine hydrochloride and auxiliary material was used. The total amounts of the filling material of the individual 40 mg capsules used amounted to 0.2192-0.2227 g (minimum-maximum). The filling material, consisting of small globules, was ground in a mortar with pistil. Thereafter the grounded material was suspended in hydroxyethylcellulose (0.5%) in demineralised water. The suspensions were placed on a magnetic stirrer before and during dosing procedures for 10 minutes. The suspensions were freshly prepared in the morning and applied intraduodenally in a volume of 0.4 ml/100 g body weight to rats. Control rats received the same amount of hydroxyethylcellulose (0.5%) i.d.

2.4 Experimental Procedure

Female Sprague Dawley rats (200-270 g) were anaesthetised by a subcutaneous injection of urethane (1.25 g/kg). The body temperature was maintained at 37° C. by means of an heated small operating table and 2 red light heating lamps. The left carotid artery was prepared and a catheter for continuous blood pressure measurement was inserted and connected to a Statham pressure transducer (Model P23 Db) and connected with a computer-controlled physiological recorder (PMS PR 800, Mumed Systems Ltd London, GB).

For intraduodenal drug administration a polyethylene catheter was inserted into the upper part of the duodenum, about 5 cm downwards from the pylorus and fixed with a purse-string suture. Bilateral ureters were ligated proximally to the bladder to prevent the bladder filling with urine. Urine of the kidneys was drained onto cotton swabs within the abdomen. The urinary bladder was catheterised via the urethra by use of PE 50 polyethylene tubing filled with physiological saline and secured in place by a ligature at the lower part of the urethra. Using a "T"-connector, the bladder catheter was connected to a Statham pressure transducer (Model P23 Db) connected with the physiological recorder (PMS PR 800) to measure intravesicular pressure and to a Infusion pump (TSE, FRG). Continuous recordings of intravesicular pressure and arterial blood pressure were captured onto a 4 channel Linearcorder WR3310 (Western Graphtec, Inc., USA). The experiment was started infusing (0.05 ml/min) the bladder with warmed saline (37-38° C.) to evoke rhythmic bladder contractions by means an infusion pump up to a maximal volume of 1.0 ml. The infusion is stopped after reaching the final volume or with the start of rhythmic bladder contractions.

Following a 15 min period of isovolumetric, rhythmic bladder contractions intraduodenal (0.4 mL/10 g bw) drug administration was performed. The continuous registration lasted 1 hr. The amplitude of the urinary bladder contractions was evaluated for 5 min before (baseline) and up to 60 min after substance administration in intervals of 15 min each. The frequency was evaluated for 10 min before (baseline) and within the observation period in intervals of 10 minutes starting 5, 20, 35 and 50 min after drug administration. For intraduodenal dosing, drugs were administered via a duodenal polyethylene tube to animals in aqueous suspension of 0.5% hydroxyethylcellulose.

3 Results

The rapid distension of the urinary bladder by filling them with warmed physiological solution in urethane anaesthetised rats produced a series of rhythmic bladder voiding contractions. By examining the cystometrograms of a number of animals (25 animals) we observed, that the mean basal frequency of the voiding contractions was 0.81 peaks/min (8.1 peaks in 10 min of observation, range 6-13 peaks). The mean value of the amplitude of the basal peaks was 31.0 mm Hg (range 16-48 mm Hg). The basal mean arterial blood pressure amounted to 91.4 mm Hg (range 75-128 mm Hg).

In 4 control rats used for evaluation of flupirtine maleate and oxybutynin hydrochloride intraduodenal administration of vehicle (0.4 mL/100 g bw hydroxyethylcellulose 0.5%) had no clear inhibitory effects on bladder contractions in the observation period of 1 hour. 2-4 times lack of a single amplitude or maximally 6 min absence of voiding-contractions were observed in 3 control animals. The mean contraction amplitude maximally decreases on average by 11% without changing the voiding frequency over the time period (by −3%). The mean arterial blood pressure decreases by 10% (see table 1).

In 6 control rats used for evaluation of duloxetine hydrochloride intraduodenal administration of vehicle (0.4 mL/100 g bw hydroxyethylcellulose 0.5%) had no clear inhibitory effects on bladder contractions in the observation period of 1 hour. 1-4 times lack of a single amplitude or maximally 6 min absence of voiding-contractions were observed in 3 control animals. The mean contraction amplitude maximally decreases on average by 12% combined by a slight reduction of the voiding frequency over the time period (by 13%). The mean arterial blood pressure decreases by 11% (see table 2).

Tables 3 and 4 show the effects of flupirtine maleate, oxybutynin hydrochloride and duloxetine hydrochloride, respectively, with regard to the presence or absence of bladder contractions, influence on voiding frequency and pressure amplitude of each animal tested in a 55 min time period (starting 5-8 min after intraduodenal administration of either vehicle or drug suspension).

Figure 2:
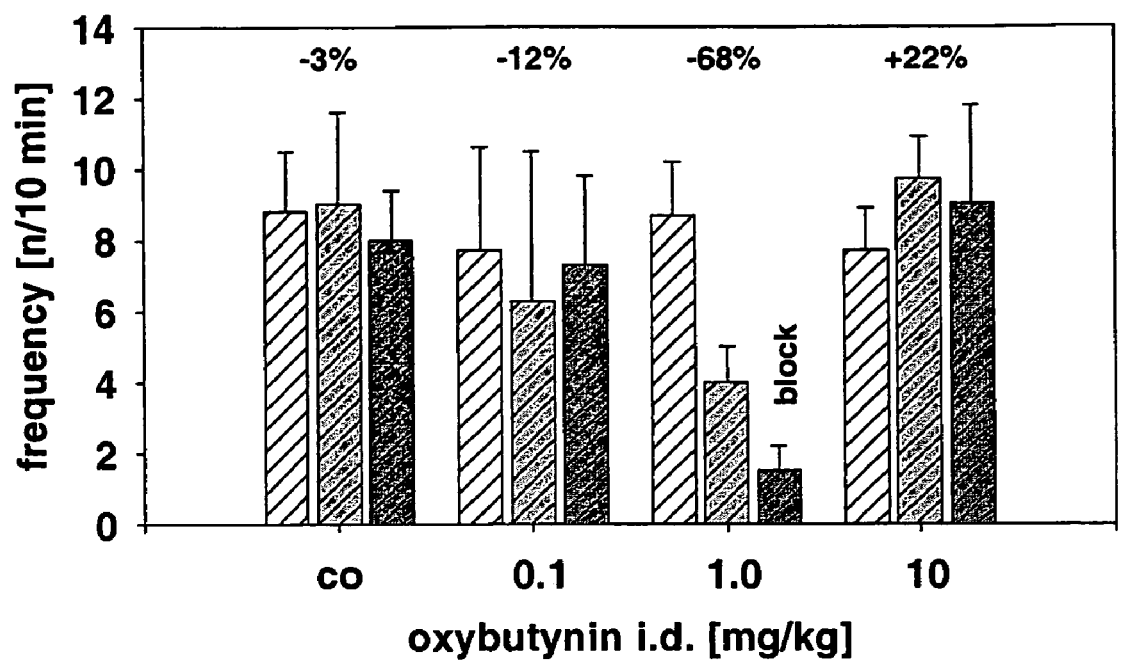
FIG. 2: Effects of different i.d. doses of oxybutynin hydrochloride on the frequency [n/10 min] (A) and the amplitude [mm Hg] (B) of the rhythmic bladder contractions. Bars represent the mean number of peaks [n/10 min]=frequency (upper, hatched bars), or the mean height of the peaks [mm Hg]=amplitude (lower, non hatched bars) with their standard deviations (sd), recorded 'pre'=☐ and 'post'=▨ 20-30 min; ■ 50-60 min, co=control group. Values above the bars are mean change in percent from base value (Δ%).
Figure 2:
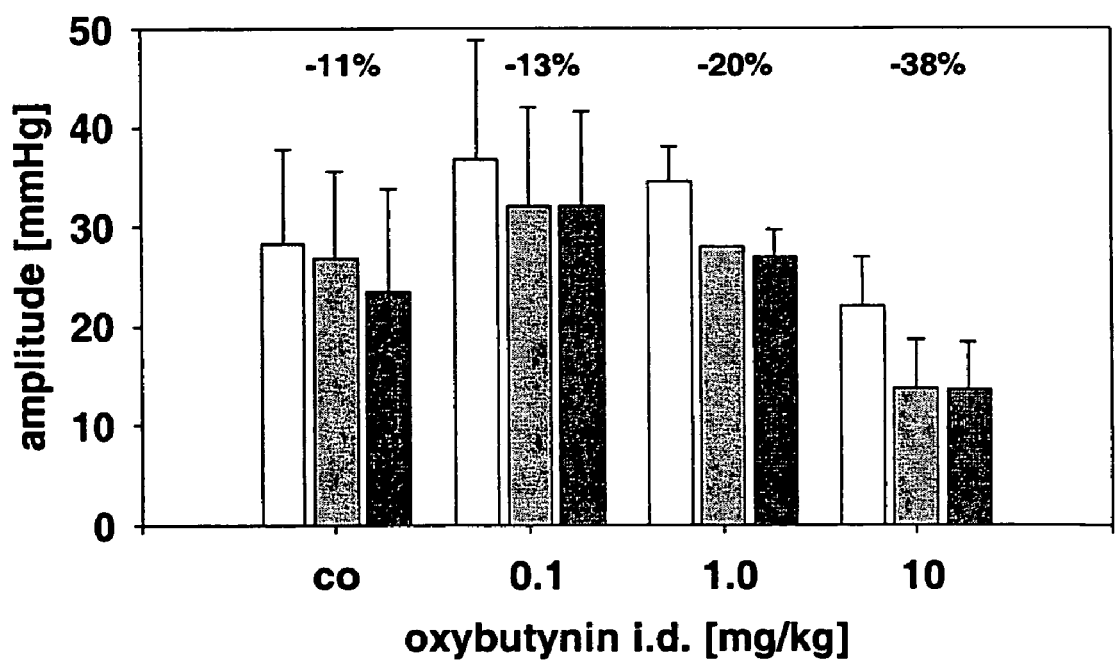
Figure 3:
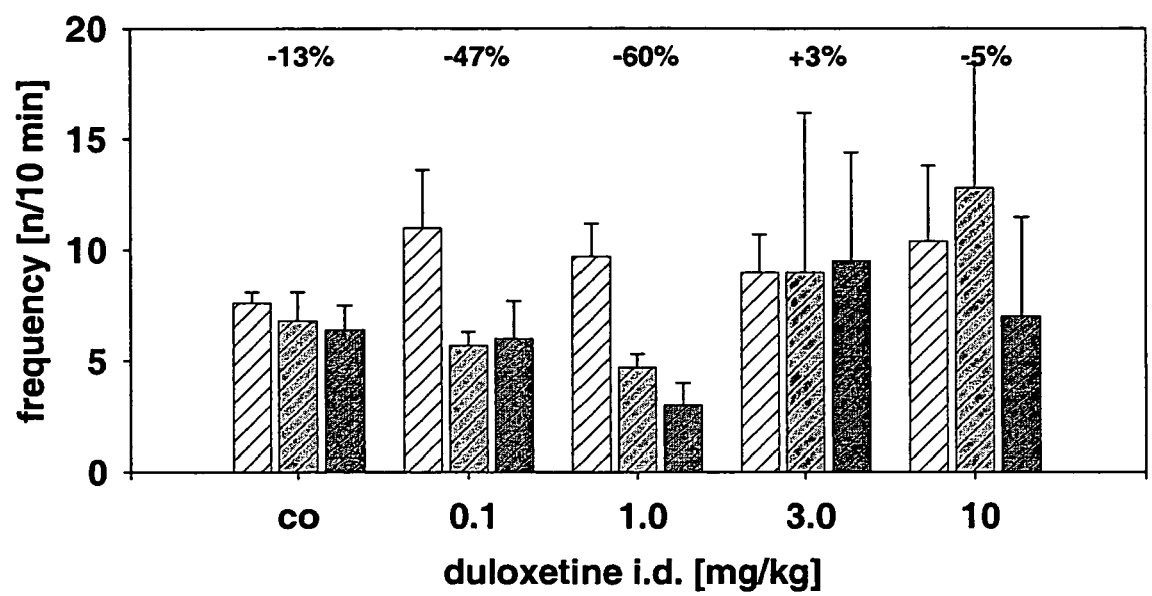
FIG. 3: Effects of different i.d. doses of duloxetine hydrochloride on the frequency [n/10 min] (A) and the amplitude [mm Hg] (B) of the rhythmic bladder contractions. Bars represent the mean number of peaks [n/10 min]=frequency (upper, hatched bars), or the mean height of the peaks [mm Hg]=amplitude (lower, non hatched bars) with their standard deviations (sd), recorded 'pre'=☐ and 'post'=▨ 20-30 min; ■ 50-60 min, co=control group. Values above the bars are mean change in percent from base value (Δ%).
Figure 3:
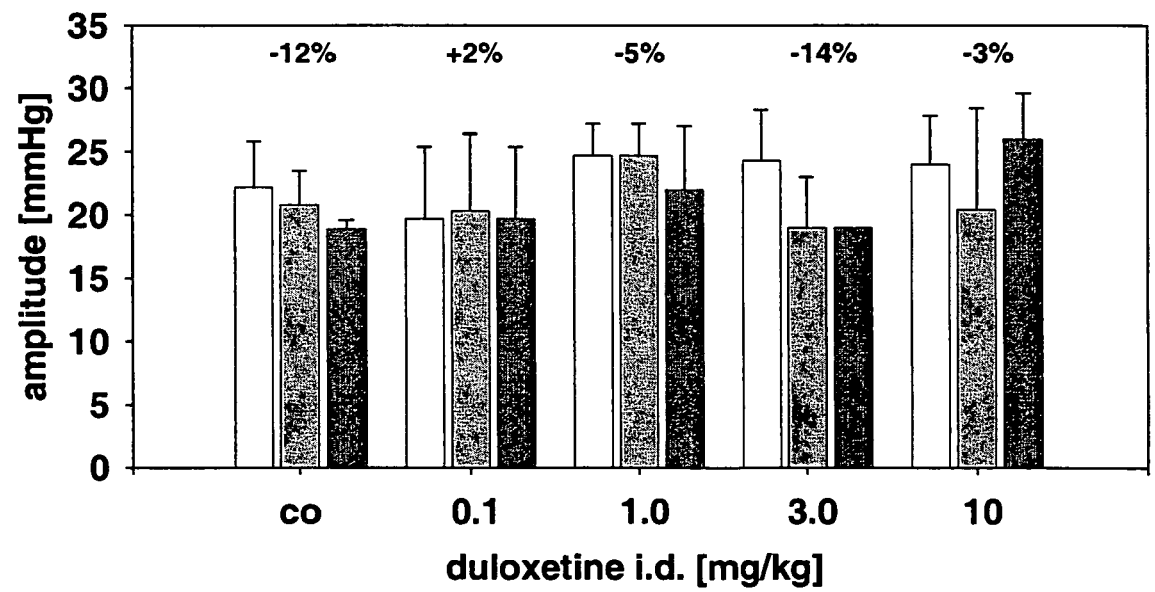

FIGS. 1-3 show the effects of different i.d. doses of flupirtine (1), oxybutynin (2) or duloxetine (3) on the mean frequency and the mean amplitude of the rhythmic bladder contractions in anaesthetised rats.

Flupirtine maleate, oxybutynin hydrochloride and duloxetine hydrochloride were tested at the dose range 0.1-10 mg/kg by intraduodenal drug administration as suspensions in aqueous tylose. In lower doses the onset of the drug action occurred mainly within 3-5 min resulting in a plateau effect of 20-30 min after drug administration. At higher doses very often the voiding contractions were fully blocked with varying length of the time interval starting 3-5 min after drug administration (see tables 3 and 4 as well as FIGS. 1-3).

Flupirtine maleate 0.1 mg/kg i.d. induced a short block of bladder contraction in 2 out of 3 animals (duration 4 or 8 min, respectively). No effect on frequency or amplitude of the remaining contractions could be observed.

At the dose 1 mg/kg i.d. flupirtine maleate lead to a short block of bladder contraction in 2 out of 3 animals. In one animal, two blocks were observed, each 4-5 min duration. In the second animal the contractions were blocked for 16 min. After re-occurrence of the contractions in these animals the frequency was reduced by 17% and 23%, respectively. The amplitude of the contractions remained unchanged. In the remaining rat flupirtine maleate (1 mg/kg i.d.) had no influence on volume-induced bladder contractions.

At the dose 3 mg/kg i.d. flupirtine maleate lead to a short block of bladder contraction in all three animals tested (duration 5-14 min) combined with a marked decrease in the mean voiding frequency by 40% of the re-occurring contractions. In one animal a second episode of contraction block could be observed at the end of the observation period. The amplitude of the voiding contractions remained unchanged.

At the dose 10 mg/kg i.d. flupirtine maleate abolished voiding contractions in 1/3 animals over the whole observation period. In the other two rats flupirtine maleate lead to a partial blockade of bladder contractions (duration 26 or 29 min) starting immediately (3-5 min) after drug administration. When the rhythmic bladder contractions reappeared (at the time interval 40-60 min), these animals showed a reduction of the amplitude of the peaks by 26% and the voiding frequency by 57%. In all 3 animals flupirtine maleate had no influence on the mean arterial blood pressure. As in control animals a slightly decrease of the blood pressure was observed (by 11%) which therefore could not be attributed to the drug treatment.

Oxybutynin hydrochloride 0.1 mg/kg i.d. lead to sporadic repetitive blocks of bladder contraction. In each animal 1-4 episodes of blocked voiding contractions could be observed, each lasting 4-6 min. The re-occurring contractions were decreased in the frequency. In addition, short increases of the voiding frequency were observed initially or during the observation period. The mean pressure peaks of the amplitude were slightly diminished by 13%.

At the dose 1 mg/kg i.d. oxybutynin hydrochloride induced sporadic repetitive blocks of bladder contraction (3-6 episodes of block, duration of 4-30 min). In 2/3 animals this was combined with a marked decrease in the mean frequency of the remaining contractions by 68%. In the remaining rat two voiding blocks were observed (2 times, duration 9 and 30 min), starting 3 and 30 min after drug administration. In this animal, the voiding contraction did not re-appear at the end of the observation period. The mean pressure peak amplitude was reduced by 20%.

Oxybutynin hydrochloride (10 mg/kg i.d.) lead to sporadic repetitive blocks of bladder contraction (minimal to maximal duration 4-30 min) in all animals tested. In all 3 animals in addition intermittently episodes with increased contraction frequencies were observed. The mean frequency averaged over all animals tested was increased by 22%. The mean pressure peaks of the amplitude were maximally reduced by 38%. With oxybutynin hydrochloride a slight fall of the mean arterial blood pressure was observed (by 24%).

Duloxetine hydrochloride 0.1 mg/kg i.d. (n=3 animals per group) lead to sporadic repetitive blocks of bladder contractions. In each animal 2-4 episodes of blocked voiding contractions could be observed, each lasting 2-5 min (minimum-maximum). The mean frequency averaged over all animals tested was decreased by 47%. The mean pressure peaks of the amplitude remained at the same level (slightly increased by 1.7%). The mean arterial blood pressure was not influenced by the drug (slightly decreased by 15%).

At the dose 1 mg/kg i.d. duloxetine hydrochloride (n=3 animals per group) induced sporadic repetitive blocks of bladder contraction (1-6 episodes of block, duration of 2.5-10 min). In 1/3 animals this was combined with a marked decrease in the mean frequency of the voiding contractions by 70%. In two rats the re-occurring contractions after blockage showed short increases of the voiding frequency (repetitive bursts) initially or during the observation period. The mean frequency averaged over all animals tested was decreased by 60%. The mean pressure peaks of the amplitude were slightly diminished by 5.4%. The mean arterial blood pressure was not influenced by the drug (slightly decreased by 1.8%).

At the dose 3 mg/kg i.d. duloxetine hydrochloride (n=3 animals per group) induced sporadic repetitive blocks of bladder contraction (1-2 episodes of block, duration of 5-28 min). Two of the three animals react with intermittent episodes with increased contraction frequencies. In the remaining rat the voiding frequency decreased slowly and led to complete cessation of the bladder contractions starting from the 32nd up to 60th min. The height of the amplitude remained unchanged. The mean frequency averaged over all animals tested was slightly increased (by 2.8%). The mean pressure peaks of the amplitude were diminished by 14%. The mean arterial blood pressure was not influenced by the drug (slightly decreased by 11%).

Duloxetine hydrochloride (10 mg/kg i.d.) led to sporadic repetitive blocks of bladder contractions (minimal to maximal duration 2-10 min) in 4/5 animals tested. In this four animals in addition intermittently episodes with increased contraction frequencies as well as repetitive micro-contractions (repetitive bursts) or degenerative irregular contractions could be observed. The mean blood pressure increased over the whole observation period. In the remaining rat the high dose of duloxetine (10 mg/kg) led to a strong increase in the frequency with maximum value by 110% in the time period 20-30$^{th}$ min after drug administration i.d. Five minutes later, at the time point 35$^{th}$ min, a reduction of the height of the amplitude started and blockage of the voiding contractions was observed. This effect on the voidings was combined with the fall of mean arterial blood pressure to 0 mm Hg and exitus of the animal in the 60$^{th}$ min.

The mean frequency averaged over all animals tested was slightly decreased by 4.8%. The mean pressure peaks of the amplitude were slightly diminished by 3.4%. This high dose of duloxetine hydrochloride led to a consistent increase in the mean arterial blood pressure (on average by 21%).

In conclusion: The treatment of animals by a single dose of flupirtine maleate in the range of 0.1-10 mg/kg i.d. (0.24-23.7 μmol/kg i.d.) caused a dose-dependent block of the voiding contractions. The frequency of the re-occurring voiding contractions was dose dependently reduced. This effect was not accompanied with a reduction of the pressure amplitude of the voiding contractions up to a dose of 3 mg/kg i.d. in urethane anaesthetised female rats. At the high dose 10 mg/kg i.d. the voiding contractions were blocked with varying time period starting 3-5 min after drug administration. In addition, 10 mg/kg i.d. decreased the peaks of the amplitude by 26% and the voiding frequency by 57%. The efficacy of the centrally acting analgesic flupirtine maleate on the bladder function is comparable in potency to that of oxybutynin hydrochloride, a muscarinergic spasmolytic drug, but with a different profile of action avoiding sporadic increases in contraction frequency and without a strong effect on the amplitude of the voiding contractions. Duloxetine hydrochloride, which exhibits a centrally acting compound as well, was also very active in this model, but increasing the dose lead again, as already seen with oxybutinin hydrochloride, to an increase in frequency of small irregular bladder contractions which is not envisioned as acceptable drug effect but rather as unwanted side effect.

As can be learned from these results, flupirtine thus can be seen to be not only as effective as but also not inducing the unwanted effects on the bladder as observed for both, a drug acting directly on the muscarinic receptors of the bladder and a drug acting on the central control mechanisms of micuration.

TABLE 1

Effects of flupirtine maleate and oxybutynin hydrochloride on volume-induced rhythmic urinary bladder contractions (amplitude/frequency) and mean arterial blood pressure as well as blockade of bladder contraction in urethane anaesthetised rats after single intraduodenal administration

| treatment | | amplitude [mm Hg] | | frequency [n/10 min] | | mean BP [mm Hg] | | block |
|---|---|---|---|---|---|---|---|---|
| n = 3-4 per group | | Pre | Post (30-60 min) | Pre | Post (20-60 min) | Pre | Post (30-60 min) | X/n min |
| control | mean | 28.3 | 26.8-23.5 | 8.8 | 9.0-8.0 | 98.5 | 95.5-82.0 | 2/4 |
| (vehicle i.d.) | ± sd | 9.5 | 8.7-10.3 | 1.7 | 2.6-1.4 | 7.2 | 7.4-13.4 | block |
| | Δ % | 0 | −11 | 0 | −3 | 0 | −10 | 4-6 |
| flupirtine | mean | 31.7 | 29.0-28.7 | 8.7 | 10.3-7.7 | 85.3 | 85.3-76.0 | 2/3 |
| maleate | ± sd | 6.8 | 7.9-8.7 | 4.0 | 1.5-5.1 | 15.4 | 15.4-16.5 | block |
| 0.1 mg/kg i.d. | Δ % | 0 | −9.0 | 0 | +3.4 | 0 | −4.7 | 4-8 |
| flupirtine | mean | 38.0 | 37.0-36.7 | 7.7 | 7.0-7.0 | 91.7 | 89.3-81.3 | 2/3 |
| maleate | ± sd | 5.6 | 5.6-3.8 | 2.9 | 3.5-3.5 | 10.4 | 15.0-22.5 | block |
| 1.0 mg/kg i.d. | Δ % | 0 | −3.1 | 0 | −8.7 | 0 | −6.9 | 4-18 |
| flupirtine | mean | 27.5 | 26.3-26.3 | 8.7 | 5.7-4.7 | 87.7 | 80.0-75.3 | 3/3 |
| maleate | ± sd | 2.2 | 2.1-2.1 | 2.1 | 1.5-2.1 | 11.7 | 10.0-13.7 | block |
| 3.0 mg/kg i.d. | Δ % | 0 | −4.2 | 0 | −40 | 0 | −12 | 5-14 |
| flupirtine | mean | 30.3 | — 22.3 | 7.0 | — 3.0 | 91.7 | 79.3-83.3 | 3/3 |
| maleate | ± sd | 9.3 | — 8.1 | 1.0 | — 2.0 | 2.9 | 9.0-5.8 | block |
| 10 mg/kg i.d. | Δ % | 0 | 3/3 CB −26 | 0 | 3/3 CB −57 | 0 | −11 | 26-56 |
| oxybutynin | mean | 36.7 | 32.0-32.0 | 7.7 | 6.3-7.3 | 79.3 | 77.7-72.7 | 3/3 |
| hydrochloride | ± sd | 12.1 | 10.0-9.5 | 2.9 | 4.2-2.5 | 9.0 | 15.7-15.5 | block |
| 0.1 mg/kg i.d. | Δ % | 0 | −13 | 0 | −12 | 0 | −5 | 4-6 |
| oxybutynin | mean | 34.5 | 28.0-27.0 | 8.7 | 4.0-1.5 | 97.5 | 80.0-85.0 | 3/3 |
| hydrochloride | ± sd | 3.5 | — 2.8 | 1.5 | 1.0-0.7 | 3.5 | 21.2-0 | block |
| 1.0 mg/kg i.d. | Δ % | 0 | 3/3 bl −20 | 0 | 3/3 bl −68 | 0 | −15 | 10-30 |
| oxybutynin | mean | 22 | 13.7-13.5 | 7.7 | 9.7-9.0 | 99.3 | 83.3-68.3 | 3/3 |
| hydrochloride | ± sd | 5.0 | 5.0-4.9 | 1.2 | 1.2-2.8 | 24.8 | 14.4-7.6 | block |
| 10 mg/kg i.d. | Δ % | 0 | −38 | 0 | +22 | 0 | −24 | 5-30 |

Legend:
Data are presented as mean ± sd, pre and post compound administration in a 20-60 min or 30-60 min time period and change in percent from base value (Δ %)
CB = complete blockade with or without isolated contractions (contractions were abolished)
block = blockade (min duration)
mean BP = mean arterial Blood Pressure

TABLE 2

Effects of duloxetine hydrochloride on volume-induced rhythmic urinary bladder contractions (amplitude/frequency) and mean arterial blood pressure as well as blockade of bladder contraction in urethane anaesthetised rats after single intraduodenal administration

| treatment | | amplitude [mm Hg] | | frequency [n/10 min] | | mean BP [mm Hg] | | block |
|---|---|---|---|---|---|---|---|---|
| n = 3-5 per group | | Pre | Post (30-60 min) | Pre | Post (20-60 min) | Pre | Post (30-60 min) | X/n min |
| control | mean | 22.2 | 20.8-18.9 | 7.6 | 6.8-6.4 | 92.2 | 82.2-82.8 | 5/5 |
| (vehicle i.d.) | ± sd | 3.6 | 2.7-0.7 | 0.5 | 1.3-1.1 | 17.6 | 21.0-14.6 | block |
| | Δ % | 0 | −12 | 0 | −13 | 0 | −11 | 2-6 |
| duloxetine | mean | 19.7 | 20.3-19.7 | 11.0 | 5.7-6.0 | 98.7 | 84.3-82.7 | 3/3 |
| hydrochloride | ± sd | 5.7 | 6.1-5.7 | 2.6 | 0.6-1.7 | 4.0 | 7.5-6.4 | block |
| 0.1 mg/kg i.d. | Δ % | 0 | +1.7 | 0 | −47 | 0 | −15 | 2.5-5 |
| duloxetine | mean | 24.7 | 24.7-22.0 | 9.7 | 4.7-3.0 | 78.3 | 77.7-76.3 | 3/3 |
| hydrochloride | ± sd | 2.5 | 2.5-5.0 | 1.5 | 0.6-1.0 | 12.6 | 17.5-19.0 | block |
| 1.0 mg/kg i.d. | Δ % | 0 | −5.4 | 0 | −60 | 0 | −1.8 | 2.5-10 |
| duloxetine | mean | 24.3 | 22.7-19.0 | 9.0 | 9.0-9.5 | 91.7 | 93.7-70.3 | 3/3 |
| hydrochloride | ± sd | 4.0 | 4.0-0 | 1.7 | 7.2-4.9 | 15.3 | 16.8-17.8 | block |

TABLE 2-continued

Effects of duloxetine hydrochloride on volume-induced rhythmic urinary bladder contractions (amplitude/frequency) and mean arterial blood pressure as well as blockade of bladder contraction in urethane anaesthetised rats after single intraduodenal administration

| treatment | | amplitude [mm Hg] | | frequency [n/10 min] | | mean BP [mm Hg] | | block |
|---|---|---|---|---|---|---|---|---|
| n = 3-5 per group | | Pre | Post (30-60 min) | Pre | Post (20-60 min) | Pre | Post (30-60 min) | X/n min |
| 3.0 mg/kg i.d. duloxetine hydrochloride | Δ % mean ± sd | 0 24.0 3.8 | −14 20.4-26.0 8.0-3.6 | 0 10.4 3.4 | +2.8 12.8-7.0 5.6-4.5 | 0 82.8 25.2 | −11 101.8-98.3 30.1-29.3 | 5-28 4/5 block |
| 10 mg/kg i.d. | Δ % | 0 | −3.4 | 0 | −4.8 | 0 | +21 | 2-10 |

Legend:
Data are presented as mean ± sd, pre and post compound administration in a 20-60 min or 30-60 min time period and change in percent from base value (Δ %)
block = blockade (min duration)
mean BP = mean arterial Blood Pressure

TABLE 3

Effects of flupirtine maleate and oxybutynin hydrochloride on rhythmic urinary bladder contractions in urethane anaesthetised rats The table shows the presence/absence of bladder contractions in a 55 min time period (starting 5-8 min after intraduodenal administration of each dose)

| Control, 0.4 mL tylose/100 g bw i.d. | | flupirtine maleate, 0.1 mg/kg i.d. | |
|---|---|---|---|
| animal no. | | animal no. (=0.24 μmol/kg i.d.) | |
| 118 | (+) 1 × short block, max. 4 min | 161 | (+) 1 × short block, max. 8 min |
| 132 | no block | 162 | no block |
| 141 | (+) 1 × short block, max. 6 min | 163 | (+) 1 × short block, max. 4 min |
| 160 | no block | | |

| oxybutynin hydrochloride, 0.1 mg/kg i.d. | | flupirtine maleate, 1.0 mg/kg i.d. | |
|---|---|---|---|
| animal no. (=0.25 μmol/kg i.d.) | | animal no. (=2.4 μmol/kg i.d.) | |
| 164 | (+) 4 × short blocks, max. 6 min, (from 5-45th min) slight decrease in frequency by 25%, 50-60th min slight increase in frequency by 17% | 145 | no block, without influence on frequency |
| 166 | (+) 1 × 5 min block, from 39 to 44th min, slight increase in frequency by 9% during 5-15th min | 146 | + 1 × 16 min block from 6 to 22nd min, slight decrease in frequency by 17% |
| 167 | (+) 4 × short sporadic blocks, max. 4 min, initial increase, afterwards decrease in frequency by 50% | 147 | (+) 2 × 4-5 min block, moderate decrease in frequency by 23% |

| oxybutynin hydrochloride, 1.0 mg/kg i.d. | | flupirtine maleate, 3.0 mg/kg i.d. | |
|---|---|---|---|
| Animal no. (=2.5 μmol/kg i.d.) | | animal no. (=7.1 μmol/kg i.d.) | |
| 153 | +++ from 3 to 11th and 30 to 60th min, 9 and 30 min block, complete cessation of bladder contractions by 100% | 157 | ++ from 3 to 16th min, 14 min block, 6 min block, starting 56th min, slight decrease in frequency by 29% |
| 154 | ++ 3 × 7-16 min sporadic blocks, decrease in mean frequency by 62% | 158 | (+) short block, max. 5 min, marked decrease in frequency by 50% |
| 156 | ++ 5 × 4-11 min sporadic blocks, decrease in frequency by 80% | 159 | + (from 2 to 18th min, 8 min block) marked decrease in frequency by 41% |

| oxybutynin hydrochloride, 10 mg/kg i.d. | | flupirtine maleate, 10 mg/kg i.d. | |
|---|---|---|---|
| Animal no. (=25.4 μmol/kg i.d.) | | animal no. (=23.7 μmol/kg i.d.) | |
| 82 | + 2 × 4 min block, slight increase in frequency by 14% | 142 | ++ from 5 to 31st min, 26 min block, marked decrease in frequency by 68% |

TABLE 3-continued

Effects of flupirtine maleate and oxybutynin hydrochloride on rhythmic urinary bladder contractions in urethane anaesthetised rats The table shows the presence/absence of bladder contractions in a 55 min time period (starting 5-8 min after intraduodenal administration of each dose)

| | | | |
|---|---|---|---|
| 85 | ++ 1 × 30 min block from 28.-60. min 2 × intense increase in frequency by 28% | 143 | +++ from 3 to 58th min, 55 min block, complete absence of contractions marked decrease in frequency by 87% |
| 86 | + 1 × 4 min block, moderate increase in frequency by 22% | 144 | +++ from 3 to 40th min, 39 min block decrease in frequency by 57% |

Legend:
no block = volume-induced rhythmic bladder contractions present during 55-60 min observation period, 2-4 times lack of a single contraction amplitude,
block = blockade, volume-induced rhythmic bladder contractions abolished over a time period
+ or (+) = contractions abolished during 5-10 min time period,
++ = contractions abolished during 10-30 min time period,
+++ = contractions abolished during 30-60 min time period
Animal no. = internal number of animal tested

TABLE 4

Effects of duloxetine hydrochloride on rhythmic urinary bladder contractions in urethane anaesthetised rats
The table shows the presence/absence of bladder contractions in a 55 min time period (starting 5-8 min after intraduodenal administration of each dose)

Control, 0.4 mL tylose/100 g bw i.d.

| animal no. | | animal no. | |
|---|---|---|---|
| 214 | (+) initial 1 × short block (6 min) | 227 | (+) 2 × short blocks (2-5 min) |
| 218 | no block | 228 | no block |
| | | 235 | (+) 2 × short blocks (2-4 min) | duloxetine hydrochloride, 0.1 mg/kg i.d. | duloxetine hydrochloride, 3.0 mg/kg i.d.

| animal no. (=0.3 µmol/kg i.d.) | | animal no. (=9 µmol/kg i.d.) | |
|---|---|---|---|
| 215 | (+) 2 × short blocks, max. 5 min, (from 24-30th min) after recurrent contractions decrease in frequency by 43% | 221 | (+) initial short block (5 min), afterwards increase in the mean frequency by 40%, slight decrease in the height of the amplitude by 24%, decrease in mean blood pressure by 13% |
| 216 | (+) 4 × short blocks, max. 3 min, decrease in mean frequency by 50%, onset of repetitive bursts of contractions with short increase in frequency during 30-60th min | 223 | ++ 2 × block, maximally 28 min from 32 to 60th min, intense decrease in frequency, the height of the amplitude unchanged |
| 217 | (+) 3 × short sporadic blocks, max. 2.5 min, initial short block (2 min), afterwards decrease in mean frequency by 39% | 224 | (+) 2 × 7-8 min block, after an initial block sporadic phases of increase in frequency, but mean frequency decreased by 15% | duloxetine hydrochloride, 1.0 mg/kg i.d. | duloxetine hydrochloride, 10 mg/kg i.d.

| animal no. (=3 µmol/kg i.d.) | | animal no. (=30 µmol/kg i.d.) | |
|---|---|---|---|
| 206 | (+) initial short block (2.5 min), afterwards decrease in mean frequency by 55%, occurrence of repetitive micro-contractions or double spikes instead of separate contractions | 208 | during 20-30th min strong increase in the frequency by 110%, after 35th min reduction of the height of the amplitude, block of the voiding contractions, combined with the fall of mean blood pressure to 0 mm Hg, 60th min exitus |
| 207 | (+) 3 × sporadic blocks, max. 10 min, initial short block (2 min), afterwards decrease in mean frequency by 50% | 209 | (+) after initial block (8 min) marked increase in frequency maximum by ~50%, irregular micro-contractions between regular spikes, slight reduction in the amplitude by 5% |

TABLE 4-continued

Effects of duloxetine hydrochloride on rhythmic urinary bladder
contractions in urethane anaesthetised rats
The table shows the presence/absence of bladder contractions in a 55
min time period (starting 5-8 min after intraduodenal administration of each dose)

| | | | |
|---|---|---|---|
| 210 | (+) 5-6 × sporadic blocks, max. 7 min, marked decrease in mean frequency by 70%, occurrence of repetitive micro-contractions, the pressure peaks of the amplitude remained unchanged | 212 | (+) 3 × sporadic short blocks, max. 2 min, during first 30 min slight reduction in mean frequency by 11%, thereafter slight increase in frequency to base value level, increase in the pressure peaks of the amplitude and mean arterial blood pressure |
| | | 219 | (+) initial short block (7 min), afterwards occurrence of repetitive micro-contractions, $24^{th}$ min degenerative contractions with a higher base level, 2 × 7 min blocks during 41 and $60^{th}$ min |
| | | 220 | + 3 × repetitive blocks, max. 10 min, after initial block (6 min) sporadic increase in frequency by 33% during 20-$30^{th}$ min |

Legend:
no block = volume-induced rhythmic bladder contractions present during 55-60 min observation period, 2-4 times lack of a single contraction amplitude,
block = blockade, volume-induced rhythmic bladder contractions abolished over a time period
+ or (+) = contractions abolished during 5-10 min time period,
++ = contractions abolished during 10-30 min time period,
+++ = contractions abolished during 30-60 min time period
Animal no. = internal number of animal tested 4 Discussion The key symptom of overactive bladder is the overactivity of the detrusor resulting in urgency to urinate in the absence of an adequate filling of the bladder. Therefore, drugs which are reducing the frequency of voiding contractions of the bladder are of special interest. However, this effect should not be accompanied by an effect on the contraction force since a full bladder contraction is necessary to achieve a full emptying of the bladder. Both, the contraction frequency and the muscular force of the detrusor, can be observed in the model of volume induced voiding contractions in the anaesthetised rat. Flupirtine maleate at the dose range 0.1-10 mg/kg i.d., was active only on the frequency of the voiding, inducing a complete cessation of bladder contractions for a time period generally related to the administered dose. When the contractions reappeared, on the other hand, contractions had the same amplitude as before drug administration (basal value). At the high dose 10 mg/kg i.d. flupirtine maleate blocked bladder contraction and after recurrence, in addition to the pronounced decrease in frequency a minor reduction in amplitude could be also seen.

Oxybutynin hydrochloride induced a decrease in the amplitude of the pressure peaks, which was often accompanied by an intermittent increase of the frequency of the remaining contractions. This frequency increase was pronounced at the dose of 10 mg/kg. The reduction in the amplitude amounted generally to no more than 60% of the basal value. At higher doses, also a full block could be observed. When the contractions reappeared, however, their amplitude was lower than that shown in the basal observation period.

Duloxetine hydrochloride (0.1-10 mg/kg i.d.) reduced the voiding frequency dose-dependently and long lastingly. The reduction in frequency was accompanied by a temporary full block of the voiding contractions which increased in duration with increasing doses in some animals. An effect on voiding frequency at low doses however was overlaid with a paradoxical frequency increase to be seen at the highest dose tested. As a result the mean frequency was not reduced at the higher doses 3.0 and 10 mg/kg i.d. due to the sporadic increase in the frequency of the voiding in 2/3 animals and 4/5 animals, respectively. The mean amplitude of the voiding contractions was not influenced at the doses 0.1, 1.0 and 10 mg/kg while at the dose of 3.0 mg/kg, which resulted in 1/3 animals a full block from 30-60 min, the mean amplitude of the 3 animals was reduced by 14%. In our tests the threshold dose of duloxetine was not reached, because already with the dose 0.1 mg/kg the frequency decreases about 47%. In further examinations the dose 0.01 mg/kg i.d. should be tested to determine the threshold dose.

In pharmacological investigations aiming at showing the clinically established analgesic dose flupirtine maleate showed first efficacy at higher doses (25-50 mg/kg p.o.) in rodents (Jakovlev et al. 1985, Arzneim. Forsch/Drug Res 35:30-43, 1985). The dose-dependent analgesic effect in the Haffner test in mice is shown at the dose range 12.5-50 mg/kg p.o., with an ED50 value of 28 mg/kg p.o. In the inflammation induced pain test (Randall-Selitto test) in rats is flupirtine maleate active with an ED50 value of 39 mg/kg p.o. In the model volume-induced contractions in urinary bladder flupirtine maleate has an therapeutic effect at the doses 1-3 mg/kg p.o. indicating 3-10 fold higher activity of flupirtine in this model. Flupirtine maleate may thus be active in humans with overactive bladder at doses below the doses used to induce analgesic effects.

Comparing flupirtine with oxybutynin and duloxetine, we can conclude that the three compounds are equipotent, however with a different profile of the pharmacological effect. The main effect of flupirtine maleate was seen affecting the voiding frequency also resulting in a temporary full block of all contractions with increase in duration with increasing doses, while oxybutynin hydrochloride and duloxetine hydrochloride also affected the frequency, however accompanied by paradoxic effects resulting in frequency increases. In addition, a central part of the activity of oxybutynin hydrochloride was found to be a reduction in the contraction amplitude indicating musculotropic spasmolytic effects which could not be seen for flupirtine maleate to the same extend. These data indicate, that flupirtine is a very interesting drug candidate for the treatment of lower urinary tract dysfunction, and in addition for the treatment of IBS.

The invention claimed is:

1. A method comprising treating, inhibiting or reducing the incidence of a lower urinary tract dysfunction of inducing or maintaining bladder control comprising administering to a mammal in need thereof a pharmacologically effective amount of flupirtine or pharmaceutically acceptable salt or amide thereof to treat, inhibit or reduce the incidence of said lower urinary tract dysfunction in the mammal.

2. The method of claim 1, wherein the lower urinary tract dysfunction is urinary incontinence.

3. The method of claim 2, wherein the urinary incontinence is selected from the group consisting of urge incontinence, urinary incontinence which is secondary to prostate hypertrophy, and urinary incontinence which is mixed urge and stress incontinence.

4. The method of claim 2, wherein the urinary incontinence is secondary to any disease resulting in bladder dysfunction, either as a part of the symptoms of the disease, or as a result of drug treatment.

5. The method of claim 1, wherein the mammal is a human.

6. The method of claim 1, wherein the mammal is a pet animal.

7. The method of claim 6, wherein the pet is a cat or dog.

8. The method of claim 1, wherein the pharmaceutically acceptable salt of flupirtine is flupirtine maleate.

9. The method of claim 1, wherein the flupirtine or pharmaceutically acceptable salt or amide thereof is administered at a daily dose of between 50 and 1000 mg per day, calculated on the basis of the free base form of flupirtine.

10. The method of claim 1, wherein the flupirtine or pharmaceutically acceptable salt or amide thereof is administered at a daily dose of between 100 and 400 mg per day, calculated on the basis of the free base form of flupirtine.

11. The method of claim 1, wherein the flupirtine or pharmaceutically acceptable salt or amide thereof is administered orally.

12. The method of claim 1, wherein the flupirtine or pharmaceutically acceptable salt or amide thereof is administered parenterally.

13. The method of claim 1, wherein the lower urinary tract dysfunction is treated.

14. The method of claim 1, wherein the lower urinary tract dysfunction is inhibited.

15. The method of claim 1, wherein the incidence of the lower urinary tract dysfunction is reduced.

16. A method comprising treating, inhibiting or reducing the incidence of irritable bowel syndrome in a mammal comprising administering to a mammal in need thereof a pharmacologically effective amount of flupirtine or pharmaceutically acceptable salt or amide thereof to treat, inhibit or reduce the incidence of irritable bowel syndrome in the mammal.

17. The method of claim 16, wherein the mammal is a human.

18. The method of claim 16, wherein the mammal is a pet animal.

19. The method of claim 18, wherein the pet is a cat or dog.

20. The method of claim 16, wherein the pharmaceutically acceptable salt of flupirtine is flupirtine maleate.

21. The method of claim 16, wherein the flupirtine or pharmaceutically acceptable salt or amide thereof is administered at a daily dose of between 50 and 1000 mg per day, calculated on the basis of the free base form of flupirtine.

22. The method of claim 16, wherein the flupirtine or pharmaceutically acceptable salt or amide thereof is administered at a daily dose of between 100 and 400 mg per day, calculated on the basis of the free base form of flupirtine.

23. The method of claim 16, wherein the flupirtine or pharmaceutically acceptable salt or amide thereof is administered orally.

24. The method of claim 16, wherein the flupirtine or pharmaceutically acceptable salt or amide thereof is administered parenterally.

25. The method of claim 16, wherein the incidence of irritable bowel syndrome is reduced.

26. The method of claim 16, wherein the irritable bowel syndrome is treated.

27. The method of claim 16, wherein the irritable bowel syndrome is inhibited.

* * * * *